United States Patent
On et al.

(10) Patent No.: US 8,663,570 B2
(45) Date of Patent: *Mar. 4, 2014

(54) STERILIZING APPARATUS AND ION GENERATING APPARATUS

(75) Inventors: Hyeon Gi On, Seoul (KR); Jun Sang Jeon, Suwon-Si (KR); Eun Ju Ha, Suwon-Si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1058 days.

This patent is subject to a terminal disclaimer.

(21) Appl. No.: 11/176,203

(22) Filed: Jul. 8, 2005

(65) Prior Publication Data

US 2006/0177360 A1 Aug. 10, 2006

(30) Foreign Application Priority Data

Feb. 4, 2005 (KR) .......................... 10-2005-0010691

(51) Int. Cl.
B01J 19/08 (2006.01)

(52) U.S. Cl.
USPC .......... 422/186.04; 422/22; 422/29; 422/186; 250/423; 250/423 R; 250/423 F; 361/231; 361/233; 361/230

(58) Field of Classification Search
USPC ......... 422/186.04, 22, 29, 186; 361/231, 233, 361/230; 250/423, 423 R, 423 F
See application file for complete search history.

(56) References Cited

U.S. PATENT DOCUMENTS

| | | | | | |
|---|---|---|---|---|---|
| 4,265,641 | A | * | 5/1981 | Natarajan | .......................... 95/79 |
| 4,559,467 | A | * | 12/1985 | Beckmann et al. | ......... 313/359.1 |
| 4,643,745 | A | * | 2/1987 | Sakakibara et al. | .............. 96/76 |
| 5,055,963 | A | * | 10/1991 | Partridge | ...................... 361/231 |
| 5,474,600 | A | * | 12/1995 | Volodina et al. | ................... 96/57 |
| 6,781,136 | B1 | * | 8/2004 | Kato | .......................... 250/423 R |
| 2004/0172847 | A1 | * | 9/2004 | Saida et al. | ....................... 34/96 |

FOREIGN PATENT DOCUMENTS

| | | |
|---|---|---|
| JP | 2001-056395 A | 2/2001 |
| JP | 2003-007426 A | 2/2003 |
| JP | 2003-123940 A | 4/2003 |
| JP | 2003-153995 A | 5/2003 |
| JP | 2003-210564 A | 7/2003 |
| JP | 2004-079273 A | 3/2004 |
| JP | 2004-192944 A | 7/2004 |
| JP | 2004-363088 A | 12/2004 |
| JP | 2005-030685 A | 2/2005 |
| JP | 2006-034946 A | 2/2006 |
| JP | 2006-034957 A | 2/2006 |

* cited by examiner

*Primary Examiner* — Xiuyu Tai
(74) *Attorney, Agent, or Firm* — Sughrue Mion, PLLC (57) ABSTRACT

A sterilizing apparatus and an ion generating apparatus, which generate sufficient amount of cations in a short period of time and also maintain the amount of ions generated at a level that is harmless to the human body. The sterilizing apparatus and the ion generating apparatus optimize the position of an electrode to maximize the generation of active hydrogen. The ion generating apparatus includes a first electrode for generating hydrogen ions and a second electrode located such that the second electrode is separated from the first electrode by a designated distance for generating electrons and superoxide anions. The hydrogen ions generated from the first electrode react with the electrons generated from the second electrode to produce hydrogen atoms, and the hydrogen atoms react with the superoxide anions generated from the second electrode to sterilize the air.

19 Claims, 13 Drawing Sheets

| 20% RH,25°C | Turbo mode | | HIGH MODE | | LOW MODE | | ULTRA LOW MODE | |
|---|---|---|---|---|---|---|---|---|
| | A | B | A | B | A | B | A | B |
| AMOUNT OF REMAINING HYDROGEN IONS($10^4$) | 7.2 | 2.4 | 4.9 | 2.0 | 2.1 | 1.3 | 0 | 0 |
| MEAN AIR VELOCITY,(m/s) | 6.4 | | 4.1 | | 2.4 | | 1.4 | |
| AIR VOLUME (m$^3$/s) | 0.15 | | 0.10 | | 0.06 | | 0.03 | |

STERILIZING APPARATUS AND ION GENERATING APPARATUS

CROSS-REFERENCE TO RELATED APPLICATION

This application claims the benefit of Korean Patent Application No. 2005-10691, filed Feb. 4, 2005, in the Korean Intellectual Property Office, the disclosure of which is incorporated herein by reference.

BACKGROUND OF THE INVENTION

1. Field of the Invention

The present invention relates to a sterilizing apparatus and to an ion generating apparatus and, more particularly, to a sterilizing apparatus and an ion generating apparatus, which generate cations and anions to sterilize air.

2. Description of the Related Art

Generally, an air purifier comprises a filter installed in a housing for filtering out various impurities, an air blast fan for transporting indoor air to the inside of the housing and discharging the air to the outside of the housing after the air passes through the filter and an anion generating apparatus for generating anions.

When the air blast fan of the air purifier is driven, the indoor air is purified through the filter and is discharged together with the anions, which are generated by the anion generating apparatus, to an indoor space. Since a conventional air purifier with an anion generating apparatus is limited when sterilizing air using only a filter and anions, an ion generating apparatus for generating cations and anions has been developed. Japanese Patent Laid-open Publication No. 2003-123940 discloses one such ion generating apparatus for generating cations and anions in detail.

In the above conventional ion generating apparatus, an alternating current (AC) is applied to two electrodes to alternately generate cations and anions, which are then supplied to an indoor space. The generated cations are hydrogen ions ($H^+$), and the generated anions are superoxide anions ($O_2^-$). When the hydrogen ions ($H^+$) and the superoxide anions ($O_2^-$) are supplied to the indoor space, hydroxyl radicals (OH) or hydrogen peroxide ($H_2O_2$) are produced. The hydroxyl radicals (OH) or hydrogen peroxide ($H_2O_2$) attach to bacteria, thereby causing an oxidation reaction, which destroys the bacteria.

However, the above conventional ion generating apparatus discharges hydrogen ions, which are harmful to the human body, into the indoor space. Accordingly, when the hydrogen ions are inhaled by a user, the hydrogen ions injure the user's health.

Further, since, in the conventional ion generating apparatus, the same electrodes alternately generate cations and anions, considerably large amounts of cations and anions bond with each other, thereby dissipating prior to performing the sterilizing action.

Moreover, since, in the conventional ion generating apparatus, the same electrodes alternately generate cations and anions, the conventional ion generating apparatus cannot generate ions in sufficient amounts required for sterilizing the air in a short period of time.

SUMMARY OF THE INVENTION

Therefore, one aspect of the invention is to provide a sterilizing apparatus and an ion generating apparatus, which generate a sufficient amount of ions in a short period of time and also maintain the amount of ions generated at a level that is harmless to the human body.

Another aspect of the invention is to provide a sterilizing apparatus and an ion generating apparatus, which optimize the position of an electrode to maximize the generation of active hydrogen.

In accordance with one aspect, the present invention provides a sterilizing apparatus comprising a cation generating portion for generating cations and an anion generating portion located such that the anion generating portion is separated from the cation generating portion by a designated distance for generating anions.

Preferably, but not necessarily, the cation generating portion may include a discharge electrode and an induction electrode, and positive high voltage may be applied between the discharge electrode and the induction electrode.

Further, preferably, but not necessarily, the anion generating portion may be a needlelike electrode, and negative high voltage may be applied to the needlelike electrode.

Preferably, but not necessarily, a point of the needlelike electrode may be installed at a position separated from the cation generating portion by a distance of 25 mm-40 mm.

Further, preferably, but not necessarily, a point of the needlelike electrode may be installed at a position having a height of 15 mm-40 mm from a plane on which the cation generating portion is placed.

Moreover, preferably, but not necessarily, the needlelike electrode may have a length of 25 mm-40 mm, and at least a portion of the needlelike electrode is disposed inline to a side surface of the cation generating portion.

In accordance with another aspect, the present invention provides an ion generating apparatus comprising a first electrode for generating hydrogen ions and a second electrode located such that the second electrode is separated from the first electrode by a designated distance for generating electrons and superoxide anions. The hydrogen ions generated from the first electrode react with the electrons generated from the second electrode to produce hydrogen atoms, and the hydrogen atoms react with the superoxide anions generated from the second electrode to sterilize the air.

Preferably, but not necessarily, the first electrode may include a discharge electrode and an induction electrode, which face each other, and the second electrode may include a needlelike electrode.

Further, preferably, but not necessarily, a point of the needlelike electrode may be disposed at a position in the range corresponding to a separation distance of 25 mm-40 mm from the first electrode and a separation height of 15 mm-40 mm from a plane on which the first electrode is placed. The needlelike electrode may have a length of 25 mm-40 mm, and at least a portion of the needlelike electrode is disposed inline to a side surface of the first electrode.

Preferably, but not necessarily, the ion generating apparatus may further comprise a cover for restricting the diffusion range of the hydrogen ions generated from the first electrode and for restricting the electrons and the superoxide anions generated from the second electrode to a designated space.

In accordance with yet another aspect, the present invention provides an ion generating apparatus comprising a cation generating portion for generating cations and an anion generating portion for generating anions. The cation and anion generating portions are disposed such that they are not located on the same plane.

Preferably, but not necessarily, the cation generating portion may be located on a plane, and the anion generating portion may be separated from the cation generating portion by a designated distance.

Further, preferably, but not necessarily, a point of the anion generating portion may be installed at a position in the range corresponding to a separation distance of 25 mm-40 mm from the cation generating portion, a separation height of 15 mm-40 mm from a plane on which the cation generating portion is placed. The anion generating portion may have a length of 25 mm-40 mm, and at least a portion of the anion generating portion is disposed inline to a side surface of the cation generating portion.

BRIEF DESCRIPTION OF THE DRAWINGS

These and/or other aspects and advantages of the invention will be readily apparent and appreciated from the following description of the embodiments, taken in conjunction with the accompanying drawings, in which.

DETAILED DESCRIPTION OF ILLUSTRATIVE, NON-LIMITING EMBODIMENTS OF THE INVENTION

Reference will now be made in detail to exemplary embodiments of the present invention, examples of which are illustrated in the accompanying drawings, wherein like reference numerals refer to like elements throughout. Exemplary embodiments are described below to explain the present invention by referring to the accompanying drawings.

Figure 1:
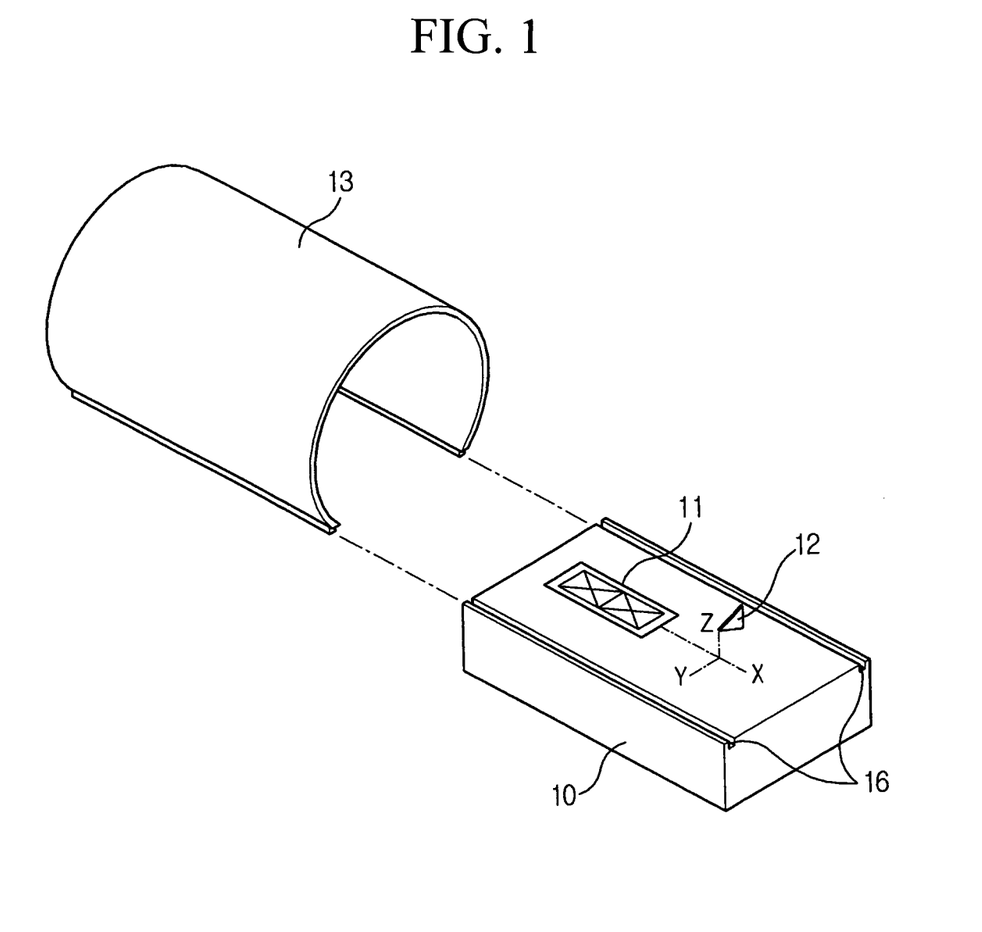
FIG. 1 is a sterilizing apparatus in accordance with an embodiment of the present invention.
Figure 2:
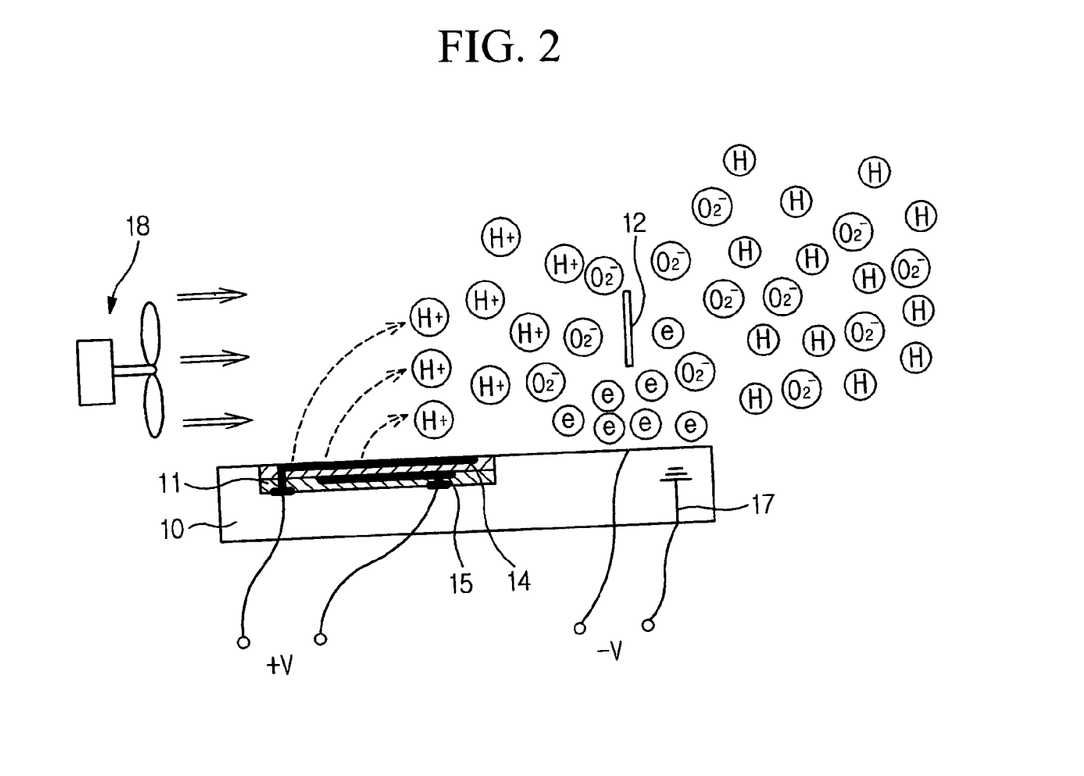
FIG. 2 is a schematic view illustrating ions generated from the sterilizing apparatus of FIG. 1.

As shown in FIGS. 1 and 2, a sterilizing apparatus in accordance with an embodiment of the present invention comprises a ceramic plate 11 installed on the upper surface of a base 10, a needlelike electrode 12 separated from the ceramic plate 11 by a designated distance so that the needlelike electrode 12 is located at a three-dimensional position, and a cover 13 for restricting the diffusion range of ions generated from the ceramic plate 11 and the needlelike electrode 12.

A depressed space for receiving the ceramic plate 11 is formed in the upper surface of the base 10, and the ceramic plate 11 is inserted into the depressed space. The ceramic plate 11 is the portion of the apparatus that generates cations. A discharge electrode 14 is disposed inside the upper portion of the ceramic plate 11, and an induction electrode 15 is disposed inside the central portion of the ceramic plate 11. Other portions of the ceramic plate 11 except for the discharge electrode 14 and the induction electrode 15 are filled with ceramic, thereby forming a protecting layer.

A positive high voltage (approximately 3.9 kV~4.3 kV) is applied between the discharge electrode 14 and the induction electrode 15. When the positive high voltage is applied between the discharge electrode 14 and the induction electrode 15, the plate 11 ionizes moisture ($H_2O$) in the air by plasma discharge, thereby generating hydrogen ($H^+$) ions.

On the other hand, a negative high voltage (approximately 3.2 kV~3.6 kV) is applied between the needlelike electrode 12 and a ground electrode 17. When the negative high voltage is applied to the needlelike electrode 12, cations are concentrated around the needlelike electrode 12 by plasma discharge, and the needlelike electrode 12 emits a large amount of electrons into the air. However, the large amount of electrons emitted into the air are unstable and are captured by oxygen ($O_2$) molecules, thereby producing superoxide anions ($O_2^-$). Accordingly, when the negative high voltage is applied to the needlelike electrode 12, the needlelike electrode 12 generates electrons and superoxide anions ($O_2^-$).

When electrons are emitted from the needlelike electrode 12, these electrons bond with hydrogen ions, which are generated from the ceramic plate 11 and pass through the periphery of the needlelike electrode 12, thereby producing hydrogen atoms (or active hydrogen). Here, in order to firmly bond the hydrogen ions generated from the ceramic plate 11 with the electrons generated from the needlelike electrode 12, an air-blowing device 18 is installed at one side of the sterilizing apparatus, and the air-blowing device 18 is driven to forcibly transfer the hydrogen ions towards the needlelike electrode 12.

As described above, since the hydrogen atoms are obtained by bonding the hydrogen ions generated from the ceramic plate 11 with the electrons generated from the needlelike electrode 12, materials that are eventually discharged from the sterilizing apparatus are hydrogen atoms and superoxide anions.

The cover 13 has a tunnel structure, and both lower ends of the cover 13 are slidably attached to and detached from cover rails 16, which are formed in both sides of the upper surface of the base 10 in a longitudinal direction. When the hydrogen ions are generated and air is blown from one side of the cover 13 with the cover 13 attached to the base 10, the hydrogen ions in the cover 13 are transported toward the needlelike electrode 12. The hydrogen ions then bond with the electrons emitted from the needlelike electrode 12, thus producing hydrogen atoms. Then, the hydrogen atoms are transported to the other side of the cover 13. Further, superoxide ions generated from the needlelike electrode 12 together with the hydrogen atoms are transported to the other side of the cover 13 by the air-blowing device 18.

Hereinafter, with reference to FIGS. 3A to 3E, a sterilizing method using the sterilizing apparatus of FIG. 1 will be described.

Hydrogen ions are generated by applying a positive high voltage between the discharge electrode 14 and the induction electrode 15 of plate 11, and electrons and superoxide anions are generated by applying a negative high voltage to the needlelike electrode 12 of plate 11. Further, the hydrogen ions are transported by the air-blowing device 18 from one side of the cover 13 so that the hydrogen ions pass through the needlelike electrode 12 or the periphery thereof.

When the hydrogen ions are close to the needlelike electrode 12, the hydrogen ions bond with electrons present around the needlelike electrode 12, thereby producing hydrogen atoms. Then, the hydrogen atoms together with the superoxide anions generated by the needlelike electrode 12 are discharged outside the cover 13 by air-blowing device 18.

Figure 3A:
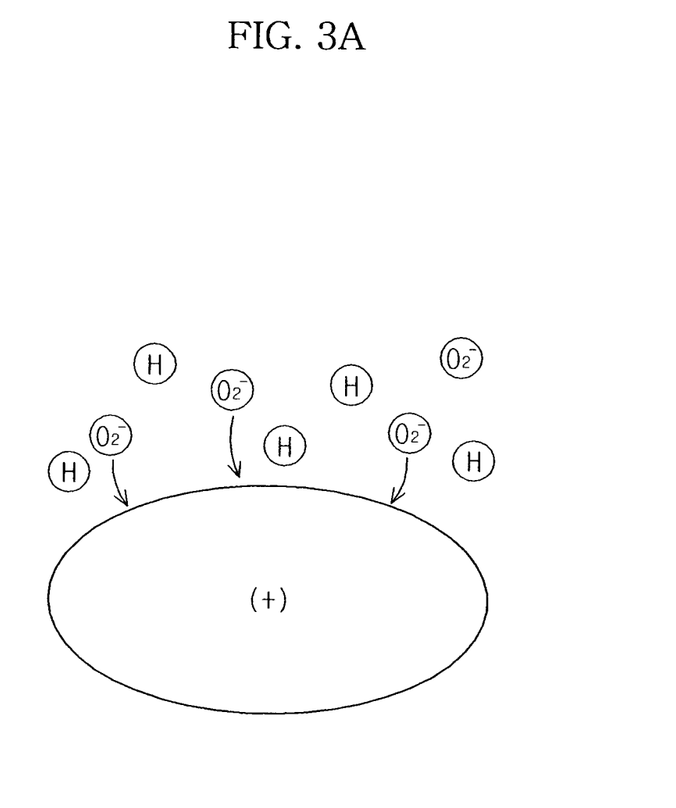
FIGS. 3A to 3E illustrate a sterilizing process using the sterilizing apparatus of FIG. 1.
Figure 3B:
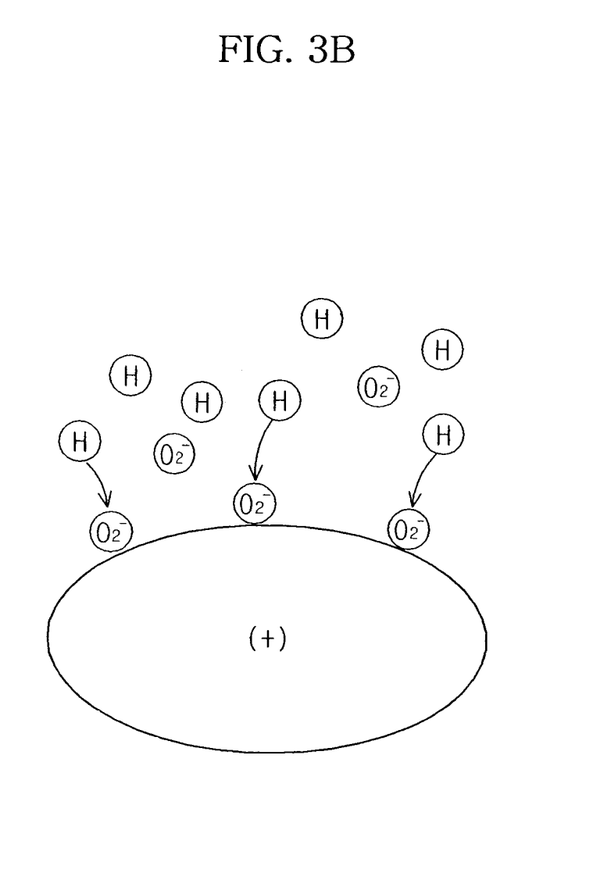
Figure 3C:
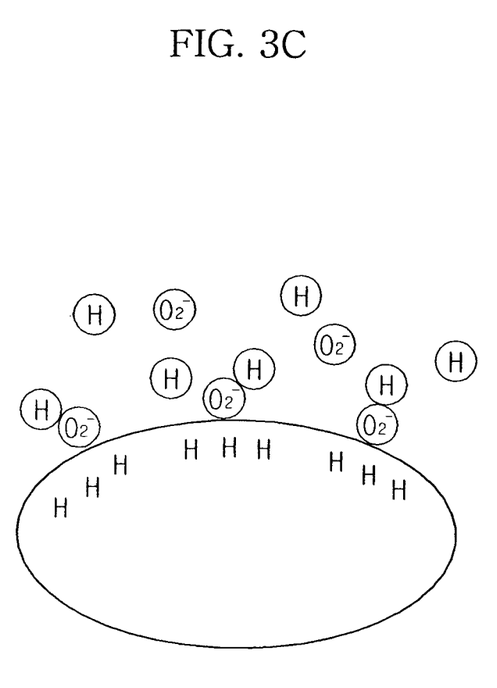

As shown in FIG. 3A, when the hydrogen atoms and the superoxide anions are discharged outside the sterilizing apparatus, the superoxide anions having a polarity opposite to that of static electricity (+) of bacteria that exist in air, and the superoxide anions attach to the surfaces of the bacteria. When the superoxide anions attach to the surfaces of the bacteria, as shown in FIGS. 3B and 3C, the hydrogen atoms attach to the superoxide anions.

Figure 3D:
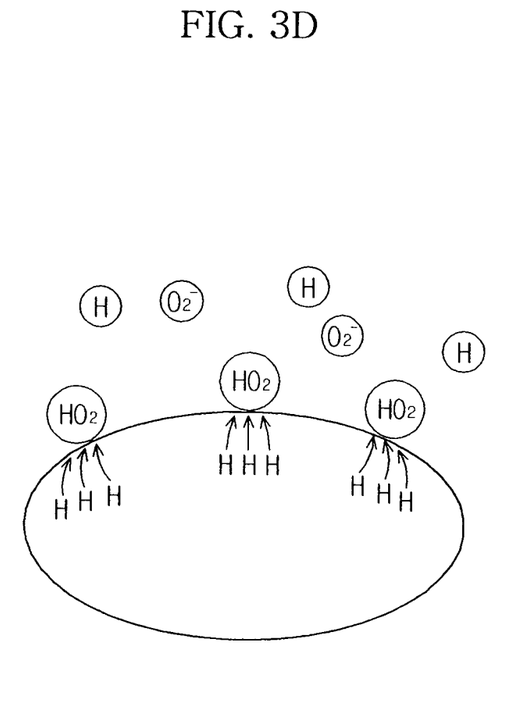
Figure 3E:
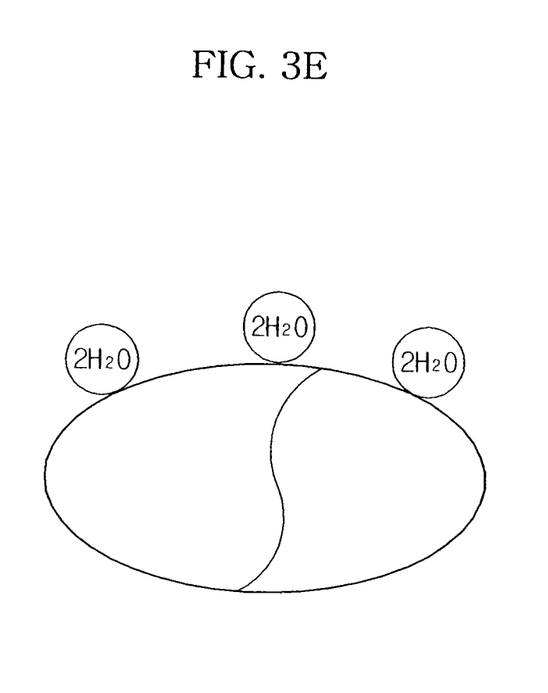

When the superoxide anions and the hydrogen atoms attach to each other, the surfaces of the bacteria are in states as shown in FIGS. 3D and 3E by means of the reaction formula given below.

$$H + O_2^- \rightarrow HO_2(\text{hydroperoxy radical}) + e + \text{static electricity of bacteria}$$

$$HO_2 + 3H(\text{hydrogen atoms of protein constituting bacterial cell membrane}) \rightarrow 2H_2O$$

That is, the superoxide anions and the hydrogen atoms, which contact each other, produce hydroperoxy radicals, and electrons of the superoxide anions offset the static electricity of bacteria. Further, the hydroperoxy radicals take three hydrogen atoms away from the protein constituting the bacterial cell membrane, thereby producing two water molecules. Then, the protein molecules of the bacterial cell membrane, which are now deprived of the hydrogen atoms, are destroyed. Accordingly, the cell membrane is destroyed and the air is sterilized.

Figure 4:
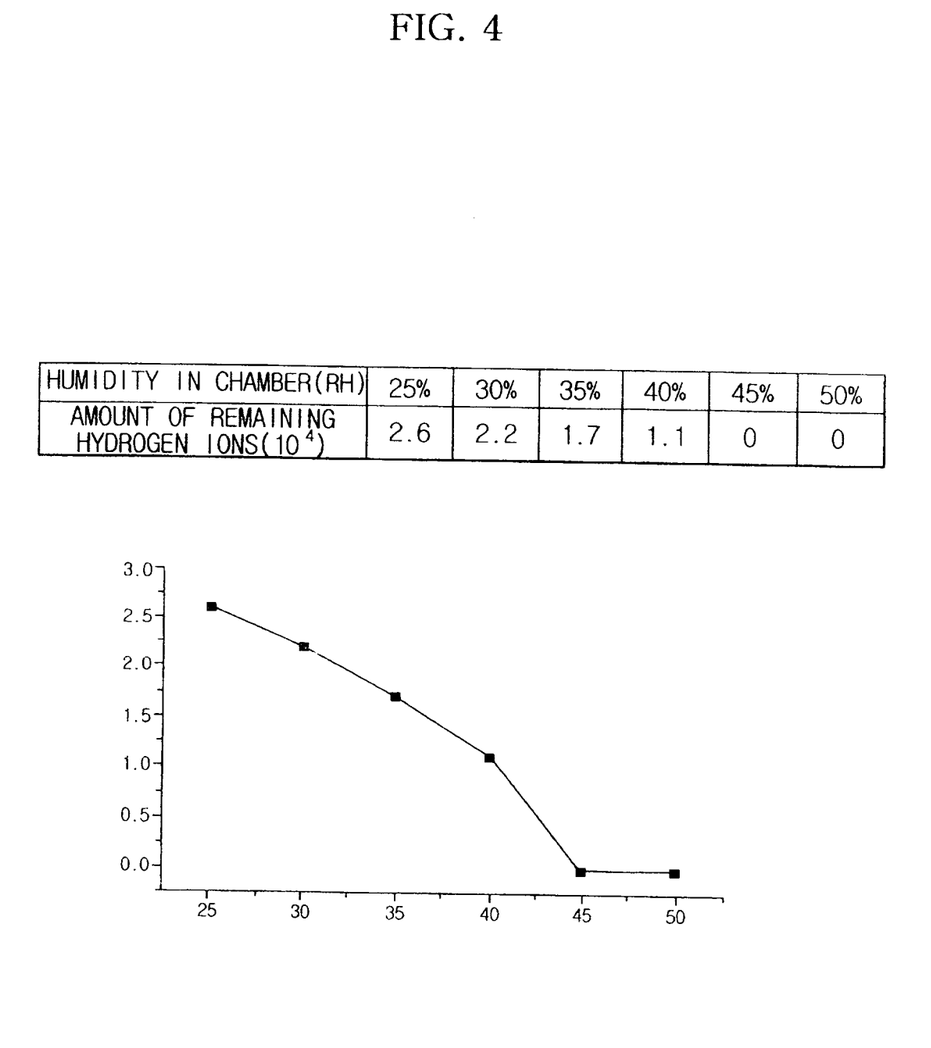
FIG. 4 is a graph illustrating variation in ionic bonding capacity according to variation in humidity.

FIG. 4 is a graph illustrating a variation in ionic bonding capacity according to a variation in humidity. FIG. 4 illustrates that the bonding rate of the electrons emitted from the needlelike electrode 12 and the hydrogen ions passing through the periphery of the needlelike electrode 12 varies according to the variation in humidity. The amount of remaining hydrogen ions after the electrons and the hydrogen ions in the sterilizing apparatus bond with each other is measured as the humidity in a test chamber (not shown) varies. As shown in FIG. 4, when the humidity in the test chamber is higher, the ionic bonding between the electrons and the hydrogen ions is easily achieved and the number of the remaining hydrogen ions is small.

The humidity in the test chamber is closely related to the air velocity (air volume). When the air velocity is high, the humidity is low. Accordingly, when the air velocity (air volume) is high, the humidity of the sterilizing apparatus is low so that the ionic bonding rate is lowered. When the air velocity (air volume) of a product is not high, such as a refrigerator or a cleaner, the humidity is not lowered. On the other hand, When the air velocity (air volume) of a product is high, such as an air cleaner or an air conditioner, the humidity is lowered, thereby creating problems in the ionic bonding capacity.

Figure 5:
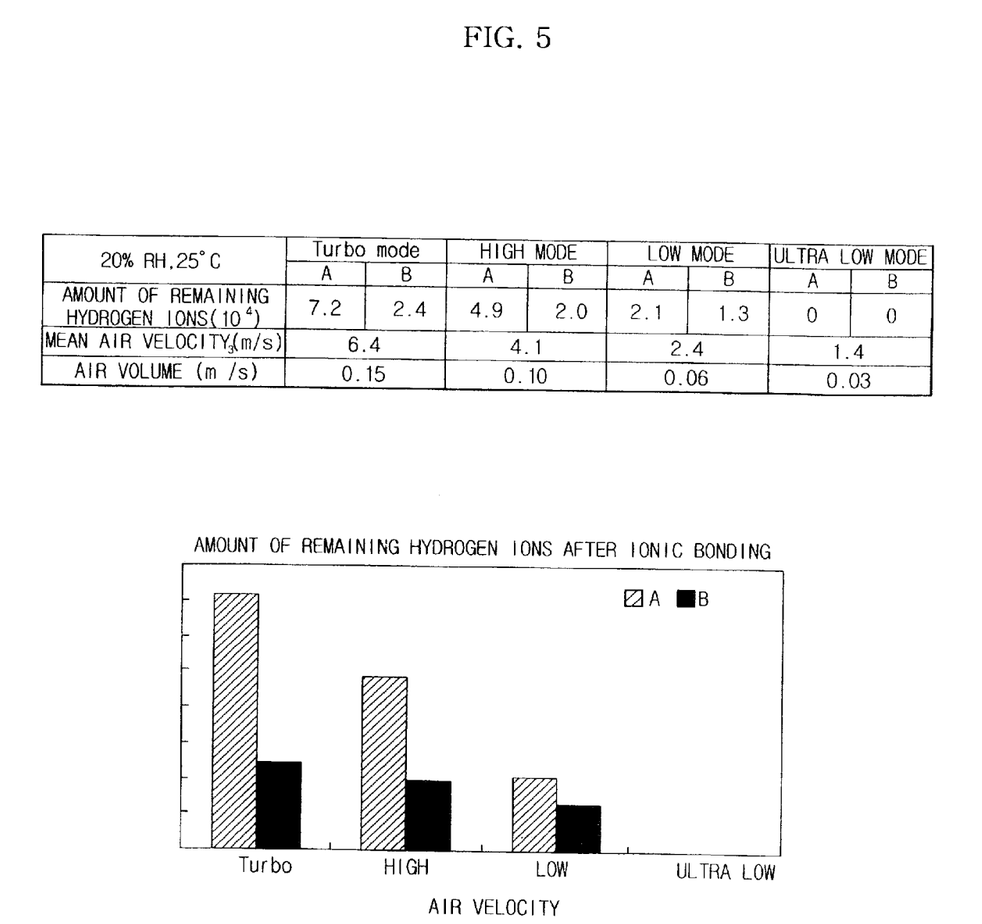
FIG. 5 is a graph illustrating variation in ionic bonding capacity according to variation in position of an electrode of the sterilizing apparatus and variation in air volume.

Therefore, it is necessary to set positions of the needlelike electrode 12 and the ceramic plate 11 so that the optimum ionic bonding capacity is maintained. FIG. 5 illustrates results of a test for setting the positions of the needlelike electrode 12 and the ceramic plate 11. In the above test, the sterilizing apparatus is applied to an air cleaner, and the amount of remaining hydrogen ions after ionic bonding was measured. Here, a model A, in which the needlelike electrode 12 is coplanar with the ceramic plate 11, and a model B, in which the ceramic plate is disposed on a plane and the needlelike electrode 12 is not disposed on the plane, were tested. During the test, the humidity in the test chamber was set to 20% RH, which lowered the ionic bonding capacity. The air velocity and the air volume were varied and amounts of remaining hydrogen ions after ionic bonding in models A and B were measured.

As shown in FIG. 5, when the air velocity and the air volume are low (LOW MODE), the ionic bonding capacity of the model A and the ionic bonding capacity of the model B were similar. On the other hand, when the air velocity and the air volume are high (TURBO MODE), the amount of remaining hydrogen ions of model A after ionic bonding was higher than that of model B after ionic bonding. That is, the ionic bonding capacity of model B was higher than the ionic bonding capacity of model A.

Figure 6:
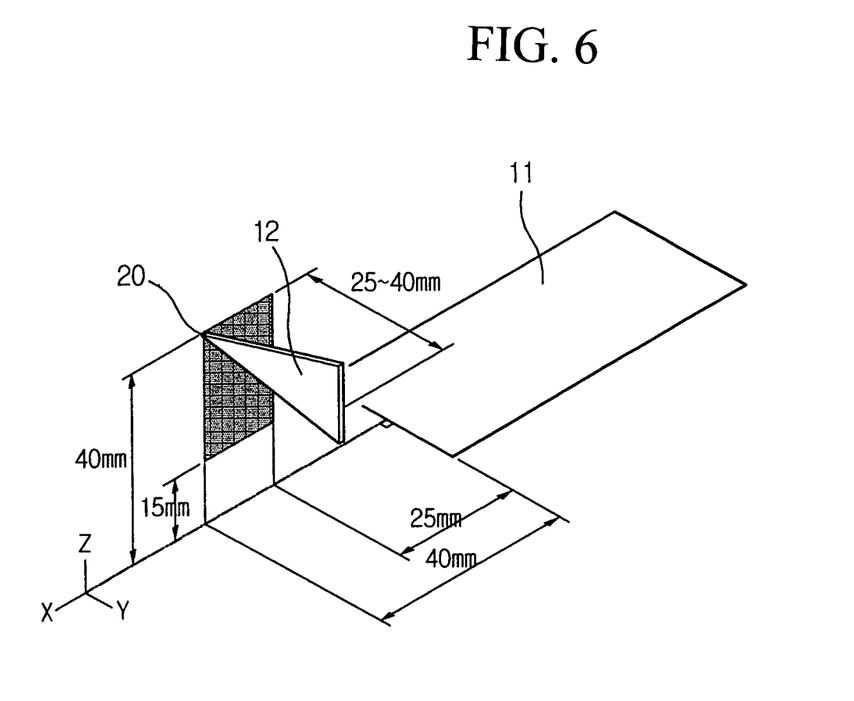
FIG. 6 is a perspective view illustrating the installation position of a needlelike electrode of the sterilizing apparatus of FIG. 1.

FIG. 6 illustrates structures of the ceramic plate 11 and the needlelike electrode 12 of model B. In model B, as shown in FIG. 6, the ceramic plate and the needlelike electrode 12 are not disposed on the same plane. A point of the needlelike electrode 12 is located on the X-axis, i.e., the central line of the ceramic plate 11, and is installed at a position in a range of a space formed by the X-axis and the Y-axis, expressed by slant lines, such that a distance of the point 20 of the needlelike electrode 12 from the ceramic plate 11 in the direction of the X-axis is 25 mm~40 mm, and a height of the point 20 of the needlelike electrode 12 from the plane, on which the ceramic plate 11 is placed, in the direction of the Z-axis is 15 mm~40 mm. Here, a length of the needlelike electrode 12 in the direction of the Y-axis is of 25 mm~40 mm.

Figure 7A:
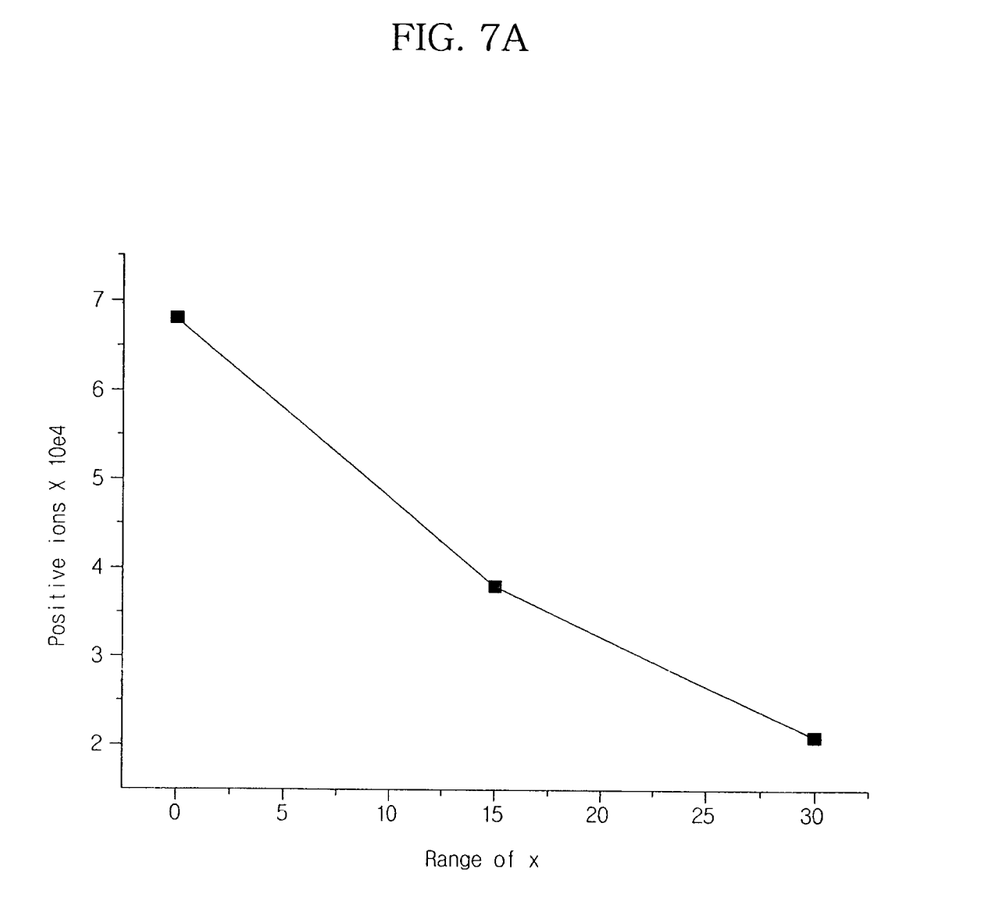
FIGS. 7A to 7C are graphs illustrating characteristics of the sterilizing apparatus of FIG. 1.
Figure 7B:
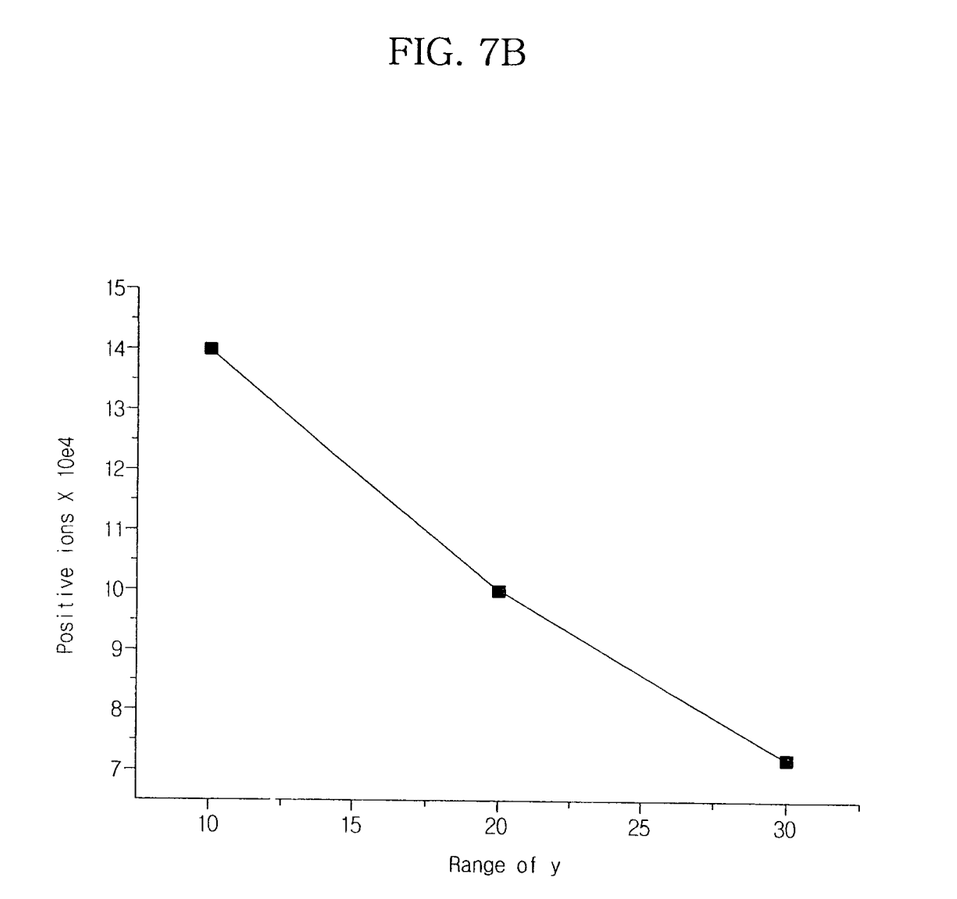
Figure 7C:
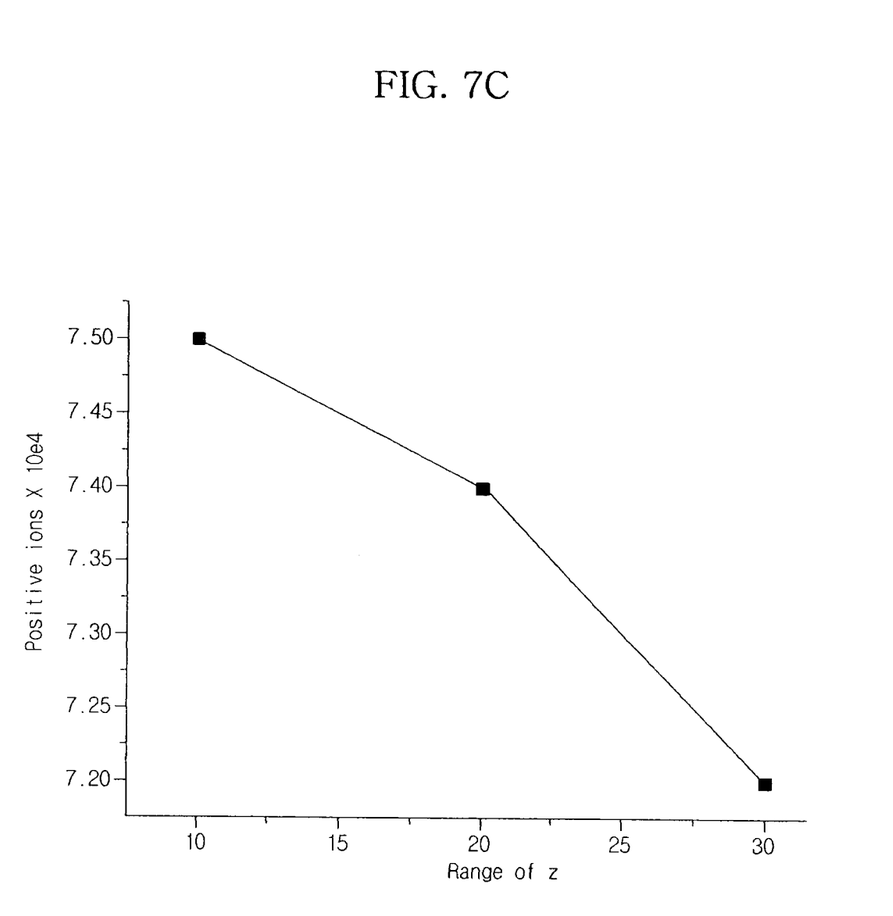

FIGS. 7A to 7C are graphs illustrating results of a test for determining the optimum three-dimensional position of the needlelike electrode 12 of FIG. 6. That is, a test was performed to set the position of point 20 of the needlelike electrode 12, which servers as the main portion for generating ions, in which the ionic bonding rate is optimum.

FIG. 7A is a graph illustrating variation in an amount of remaining hydrogen ions after ionic bonding as a function of separation distance from the ceramic plate 11 to point 20 of the needlelike electrode 12 in the direction of the X-axis. The graph in FIG. 7A shows that the ionic bonding rate is high when the separation distance from the ceramic plate 11 to point 20 of the needlelike electrode 12 is more than 25 mm. On the other hand, when the separation distance from the ceramic plate 11 to point 20 of the needlelike electrode 12 is more than 40 mm, there is a high probability of causing problems in achieving ionic bonding. Preferably, but not necessarily, the separation distance from the ceramic plate 11 to point 20 of the needlelike electrode 12 is in the range of 25 mm-40 mm.

FIG. 7B is a graph illustrating variation in an amount of the remaining hydrogen ions after ionic bonding according to a variation in a length of the needlelike electrode 12 in the direction of the Y-axis as shown in FIG. 6, when the separation distance from the ceramic plate 11 to point 20 of the needlelike electrode 12 is in the range of 25 mm-40 mm. The graph in FIG. 7B shows that the ionic bonding rate is high when the length of the needlelike electrode 12 in the direction of the Y-axis is more than 25 mm. For the same reason as that of FIG. 7A, the length of the needlelike electrode 12 in the direction of the Y-axis should not exceed 40 mm. Preferably, but not necessarily, the length of the point 20 of the needlelike electrode 12 in the direction of the Y-axis is in the range of 25 mm-40 mm.

FIG. 7C is a graph illustrating variation in an amount of the remaining hydrogen ions after ionic bonding as a function of separation height of the needlelike electrode 12 from the plane on which the ceramic plate 11 is placed in the direction of the Z-axis as shown in FIG. 6, when the separation distance from the ceramic plate 11 to point 20 of the needlelike electrode 12 is in the range of 25 mm-40 mm. The graph in FIG. 7C shows that the ionic bonding rate is high when the separation height of the needlelike electrode 12 in the direction of the Z-axis is more than 15 mm. For the same reason as that of FIG. 7A, the separation height of the needlelike electrode 12 in the direction of the Z-axis should not exceed 40 mm. Preferably, but not necessarily, the height of the needlelike electrode 12 in the direction of the Z-axis is in the range of 15 mm-40 mm.

As described above, the position of point 20 of the needlelike electrode 12 is defined by a three-dimensional positional range, i.e., the point 20 of the needlelike electrode 12 has a separation distance from the ceramic plate 11 of 25 mm-40 mm and a separation height of 15 mm-40 mm, with at least a portion of the needlelike electrode, and the needlelike electrode 12 has a length in the range of 25 mm-40 mm, disposed inline to a side of the ceramic plate 11. When the needlelike electrode is located within this positional range, the optimum ionic bonding capacity is maintained.

Although the embodiment of the present invention describes the sterilizing apparatus having the cover 13 for facilitating the reaction between hydrogen ions and electrons and the reaction between hydrogen ions and superoxide anions, the cover 13 of the sterilizing apparatus may be omitted.

As apparent from the above description, the present invention provides a sterilizing apparatus and an ion generating apparatus, which use hydrogen atoms to sterilize air instead of hydrogen ions that are harmful to the human body. Therefore, the sterilizing apparatus and the ion generating apparatus prevent a user from being exposed to the harmful hydrogen ions, as well as having a sterilizing effect.

Consistent with the present invention, the sterilizing apparatus and the ion generating apparatus may comprise a cation generating portion and an anion generating portion, which are separately installed, thereby allowing the generation of ions in amounts great enough to sterilize air in a short period of time, thus improving the sterilizing effect.

Consistent with the present invention, the sterilizing apparatus and the ion generating apparatus may comprise a needlelike electrode constituting the anion generation portion disposed such that the needlelike electrode is not on the same plane as the cation generating portion. The position of the needlelike electrode is optimized to increase the ionic bonding capacity between hydrogen ions and electrons and to maximize the amount of the hydrogen ions, thus maximizing the sterilizing power and the bacteria-removing power.

Although embodiments of the invention have been shown and described, it would be appreciated by those skilled in the art that changes may be made in this the exemplary embodiments without departing from the principles and spirit of the invention, the scope of which is defined in the claims and their equivalents.

What is claimed is:

1. A sterilizing apparatus comprising:
a base;
a cation generating portion comprising a plate disposed on the base for generating hydrogen ions;
an anion generating portion comprising a needlelike electrode for generating electrons; and
an air-blowing device configured to generate an air flow to forcibly transfer the hydrogen ions generated by the plate of the cation generating portion towards the needlelike electrode of the anion generating portion,
wherein the needlelike electrode of the anion generating portion is separated from the cation generating portion by a designated distance in a direction of an x-axis of the base and a tip of the needlelike electrode is separated from the base in a direction of a z-axis of the base,
wherein the hydrogen ions generated from the cation generating portion bond to the electrons generated from the anion generating portion to provide hydrogen atoms,
wherein the hydrogen atoms react with superoxide anions generated from the needlelike electrode to sterilize the air,
the plate includes a discharge electrode and an induction electrode, and is configured such that a positive high voltage is applied between the discharge electrode and the induction electrode, and
a negative high voltage is applied to the needlelike electrode.

2. The sterilizing apparatus as set forth in claim 1,
wherein a point of the needlelike electrode is disposed at a position separated from the cation generating portion by a distance of 25 mm-40 mm in the direction of the x-axis.

3. The sterilizing apparatus as set forth in claim 1,
wherein a point of the needlelike electrode is disposed at a position separated from a plane on which the cation generating portion is placed by a distance of 15 mm-40 mm in the direction of the z-axis.

4. The sterilizing apparatus as set forth in claim 1,
wherein the needlelike electrode has a length of 25 mm-40 mm, and at least a needlelike portion of the needlelike electrode is disposed inline to a longitudinal direction of the cation generating portion.

5. The sterilizing apparatus as set forth in claim 1, wherein:
the direction of the x-axis is parallel to a lengthwise direction of the sterilizing apparatus.

6. The sterilizing apparatus as set forth in claim 5,
wherein the discharge electrode and the induction electrode which face each other.

7. The sterilizing apparatus as set forth in claim 5,
wherein:
the needlelike electrode is disposed at a position in a range corresponding to a distance of 25 mm-40 mm from the plate in the direction of the x-axis and a height of 15 mm-40 mm from a plane, on which the plate is placed, in the direction of the z-axis; and
the needlelike electrode has a length of 25 mm-40 mm in a lengthwise direction of the plate.

8. The sterilizing apparatus as set forth in claim 5, further comprising a cover for restricting a diffusion range of the hydrogen ions generated from the plate and the electrons and the superoxide anions generated from the needlelike electrode to a designated space.

9. An ion generating apparatus comprising:
a base;
a cation generating portion comprising a plate and configured to generate hydrogen ions;
an anion generating portion comprising a needlelike electrode that generates electrons and is separated from the cation generating portion by designated distances in directions of an x-axis and a z-axis;
an air-blowing device configured to generate an air flow to transfer the hydrogen ions generated by the plate of the cation generating portion towards the needlelike electrode of the anion generating portion, wherein:
one of the cation and anion generating portions is located on the base and the other one of the cation and anion generating portions is separated from the base in the direction of the z-axis;
the direction of the x-axis is parallel to a lengthwise direction of the ion generating apparatus;
the hydrogen ions generated from the cation generating portion bond to the electrons generated from the anion generating portion to provide hydrogen atoms;

the hydrogen atoms react with superoxide anions generated from the needlelike electrode to sterilize the air the plate includes a discharge electrode and an induction electrode, and is configured such that a positive high voltage is applied between the discharge electrode and the induction electrode, and a negative high voltage is applied to the needlelike electrode.

10. The ion generating apparatus as set forth in claim 9, wherein a point of the anion generating portion is disposed at a position in a range corresponding to a distance of 25 mm-40 mm from the cation generating portion in the direction of the x-axis and a height of 15 mm-40 mm from the plane, on which the cation generating portion is placed, in the direction of the z-axis; and the anion generating portion is disposed inline to a side surface of the cation generating portion and has a length of 25 mm-40 mm.

11. A sterilizing apparatus comprising:

a base;

a cation generating portion comprising a plate disposed on the base for generating hydrogen ions;

an anion generating portion comprising a needlelike electrode for generating electrons;

an air-blowing device configured to generate an air flow to transfer the hydrogen ions generated by the plate of the cation generating portion towards the needlelike electrode of the anion generating portion; and an ion diffusion preventing cover that restricts a diffusion range of ions generated by the cation generating portion and the anion generating portion;

wherein the cation generating portion is disposed on an upper surface of the base;

wherein the anion generating portion is separated from the cation generating portion by a designated distance in a direction of an x-axis of the base and is separated from the base and the cation generating portion by a designated distance in a direction of a z-axis of the base;

wherein the direction of the x-axis is parallel to a lengthwise direction of the sterilizing apparatus, wherein the hydrogen ions generated from the cation generating portion bond to the electrons generated from the anion generating portion to provide hydrogen atoms, wherein the hydrogen atoms react with superoxide anions generated from the needlelike electrode to sterilize the air wherein the plate includes a discharge electrode and an induction electrode, and a positive high voltage is applied between the discharge electrode and the induction electrode, and wherein a negative high voltage is applied to the needlelike electrode.

12. A sterilizing apparatus comprising:

a base;

a cation generating portion comprising a plate that is disposed on the base and generates hydrogen ions;

an anion generating portion including a needlelike electrode that generates electrons; and an air blast fan that is configured to generate an air flow that transfers the hydrogen ions generated by the plate of the cation generating portion towards the needlelike electrode of the anion generating portion, wherein:

the cation generating portion and the anion generating portion are separated from each other by a designated distance, and the anion generating portion is separated from the base in a Z-axis direction, an X-axis represents a traveling direction of the air blown by the air blast fan and almost coincides with central lines of the cation generating portion and the anion generating portion in a direction of the X-axis, the hydrogen ions generated from the cation generating portion bond to the electrons generated from the anion generating portion to provide hydrogen atoms;

the hydrogen atoms react with superoxide anions generated from the needlelike electrode to sterilize the air the cation generating portion is formed a plate shape, and a positive voltage is applied the cation generation portion; and the anion generating portion is formed a needle shape, and a negative voltage is applied to the anion generating portion.

13. The sterilizing apparatus as set forth in claim 12, wherein a central line of the air blast fan in the direction of the X-axis coincides with the central lines of the cation generating portion and the anion generating portion in the direction of the X-axis.

14. The sterilizing apparatus as set forth in claim 12, wherein:

the anion generating portion generates $O_2^-$ ions in addition to generating the electrons; and the hydrogen ions bond to the electrons to produce H atoms.

15. The sterilizing apparatus as set forth in claim 12, wherein:

the cation generating portion is formed in a flat plate shape, and is mounted on the upper surface of the base; and the anion generating portion is protruded from an upper surface of the base.

16. A sterilizing apparatus comprising:

a base;

an $H^+$ ion generating portion comprising a plate disposed on the base that generates $H^+$ ions;

an electron generating portion including a needlelike electrode that is separated from the $H^+$ ion generating portion and generates electrons;

an air blast fan configured to generate an air flow to transfer the hydrogen ions generated by the plate of the $H^+$ ion generating portion towards the needlelike electrode of the electron generating portion, wherein a plane on which the $H^+$ ion generating portion is mounted and a plane on which the electron generating portion is mounted are different such that the electron generating portion is separated from the base, wherein the $H^+$ ions generated from the $H^+$ ion generating portion bond to the electrons generated from the electron generating portion to provide hydrogen atoms, wherein the hydrogen atoms react with superoxide anions generated from the needlelike electrode to sterilize the air wherein the $H^+$ generating portion includes a discharge electrode and an induction electrode, and a positive voltage is applied the $H^+$ generating portion, and wherein a negative voltage is applied between the needlelike electrode and a ground electrode separated from the needle like electrode.

17. The sterilizing apparatus as set forth in claim 16, further comprising an ion diffusion preventing cover configured to cover both the $H^+$ ion generating portion and the electron generating portion.

18. The sterilizing apparatus as set forth in claim 16, wherein the air blast fan, the $H^+$ ion generating portion, and the electron generating portion are sequentially disposed.

19. The sterilizing apparatus as set forth in claim 18, wherein an air velocity of the air blast fan is adjusted according to an amount of remaining hydrogen ions after the reaction between the $H^+$ ions generated from the $H^+$ ion generating portion and the electrons generated from the electron generating portion.

* * * * *